(12) United States Patent
Hublot et al.

(10) Patent No.: US 7,799,328 B2
(45) Date of Patent: Sep. 21, 2010

(54) METHOD FOR TREATING WEIGHT LOSS IN PATIENTS SUFFERING FROM INFLAMMATORY BOWEL DISEASES

(75) Inventors: Bernard Hublot, Compiegne (FR); Herve Groux, Biot (FR); Rene Levy, Seattle, WA (US); Marie-Emmanuelle Le Guern, Compiegne (FR); Paul Bernasconi, Paris (FR)

(73) Assignee: Biocodex, Gentilly (FR)

( * ) Notice: Subject to any disclaimer, the term of this patent is extended or adjusted under 35 U.S.C. 154(b) by 92 days.

(21) Appl. No.: 10/895,455

(22) Filed: Dec. 23, 2004

(65) Prior Publication Data
US 2006/0140973 A1 Jun. 29, 2006

(51) Int. Cl.
*A01N 63/04* (2006.01)
*C12N 1/00* (2006.01)

(52) U.S. Cl. .............................. 424/195.16; 424/93.51; 435/255.2

(58) Field of Classification Search ........................ None
See application file for complete search history.

(56) References Cited

U.S. PATENT DOCUMENTS

| 4,595,590 A | 6/1986 | Hublot et al. |
| 2002/0155126 A1 | 10/2002 | Shirasu et al. |

FOREIGN PATENT DOCUMENTS

FR 2244464 A * 5/1975

OTHER PUBLICATIONS

Guslandi, M; MD, Digestive Diseases and Sciences (Jul. 2000), 45(7): 1462-1464. *Saccharomyces boulardii* in maintenance treatment of Crohn's disease.*
Guindi, M et al. J. Clin. Pathol. (2004); 57: 1233-1244. Indeterminate colitis.*
Z Gastroenterol (Feb. 1993); 31(2): 129-134. Plein, K et al. Therapeutic effects of *Saccharomyces boulardii* on mild residual symptoms in a stable phase of Crohn's disease with special respect to chronic diarrhea—a pilot study.*
Plein, K et al. Z Gastroenterol (Feb. 1993); 31(2): 129-134. Therapeutic effects of *Saccharomyces boulardii* on mild residual symptoms in a stable phase of Crohn's disease with special respect to chronic diarrhea—a pilot study.*
Lukaczer, D. Nutrition Science News (2000). The probiotic solution for colitis. Downloaded Oct. 26, 2008. http://www.newhope.com/nutritionsciencenews/NSN_backs/Dec_00/colitis.cfm?path=print.*
Hanauer, SB et al. Clinical Therapeutics (1998). 20(5): 1009-1028. Advances in the management of Crohn's disease: economic and clinical potential of infliximab.*
Hanauer, SB et al. The American Journal of Gastroenterology (2001); 96(3): 635-643. Management of Crohn's disease in adults.*
Bleichner, G. et al. "*Saccharomyces boulardii* prevents diarrhea in critically ill tube-fed patients" Intensive Care Med (1997) 23:517-523.
Booth, I.W. et al. "Short bowel syndrome" *Baillière's Clinical Gastroenterology* vol. 12, No. 4, Dec. 1998; 12(4): 739-73.
Jahnsen, J. et al. "Body Composition in Patients With Inflammatory Bowel Disease: A Population-Based Study" The American Journal of Gastroenterology vol. 98, No. 7, 2003, pp. 1556-1562.

* cited by examiner

*Primary Examiner*—Michele Flood
(74) *Attorney, Agent, or Firm*—Young & Thompson

(57) ABSTRACT

The present invention relates to a method of treating or preventing weight loss of patients with inflammatory bowel diseases comprising administering to said patients an effective amount of *Saccharomyces boulardii*.

13 Claims, 1 Drawing Sheet

METHOD FOR TREATING WEIGHT LOSS IN PATIENTS SUFFERING FROM INFLAMMATORY BOWEL DISEASES

BACKGROUND OF THE INVENTION

The present invention relates to a therapeutic method for treating weight loss linked to inflammatory bowel diseases (IBD), such as Crohn's disease and ulcerative colitis.

Inflammatory bowel diseases are chronic relapsing conditions of the intestinal tract for which essentially no therapy is available. The major known forms of IBD are Crohn's disease and ulcerative colitis (see Carter et al. (2004) Gut 53(supplement V):v1-v16 for a review).

Crohn's disease was first described in 1932 and its prevalence is as high as 75/100,000 in Britain and Scandinavia. It mainly affects the ileon and/or the colon, with 60% of patients suffering from an ileocolonic form of the disease. Its clinical manifestations include abdominal pain, nausea, diarrhea, anorexia, abdominal tenderness, and weight loss.

Ulcerative colitis (UC) was first completely described in 1909, its prevalence is approximately 80/100,000 in the Northern world. UC affects the colonic and rectal mucosa. Among others, it is manifested by pain, diarrhea, rectal bleeding, anorexia, and weight loss.

Current treatments of IBD aim at inducing and preserving remission and mainly rely on corticosteroids, such as prednisone, aminosalicylates, such as mesalazine, immunosuppressants, and anti-TNF monoclonal antibodies, such as infliximab. If a patient fails to respond to drug therapy and relapses, a surgical intervention is usually deemed mandatory to remove the dysfunctional part of the intestinal tract.

*Saccharomyces boulardii* (*Sacharomyces cerevisiae* var. *boulardii*, Mallié et al. (2001) *J. Mycol. Med.* 11:19-25) is a thermophilic non pathogenic yeast. Clinically, *S. boulardii* is essentially used as a probiotic for short course prevention or treatment of diarrhea. It is used in particular for the management of antibiotic-associated diarrhea (McFarland et al. (1998) *Am. J. Gastroenterol.* 90:439-448) and for the prevention of *Clostridium difficile*-associated diarrhea (Surawicz et al. (2000) *Clin. Infect. Dis.* 31:1012-1017). *S. boulardii* has also been used in association with conventional drug treatment to reduce Crohn's disease-associated diarrhea (Plein and Hotz (1993) *Z. Gastroenterol.* 31:129-134).

Weight loss in inflammatory bowel disease is multifactorial. Proinflammatory cytokines (IL-1, IL-6 and TNFα) from the inflamed intestinal mucosa are known to have several effects leading to disruption of normal metabolism (Jahnsen et al. (2003) *Am. J. Gastroenterol.* 98:1556-1562). However, there are currently no therapeutic methods effective at specifically treating weight loss in IBD patients.

Thus, an object of the present invention is to provide a therapeutic method for treating weight loss in patients suffering from inflammatory bowel diseases.

SUMMARY OF THE INVENTION

The present invention follows from the unexpected finding that *Saccharomyces boulardii* could be used to treat weight loss in an animal model of inflammatory bowel disease. Furthermore, the Inventors have shown that this beneficial effect on the prevention of weight loss is parallel to a previously unrecognized specific *Saccharomyces boulardii*-induced lowering of the inflammatory lesions of the intestinal tract, which is fundamentally different from the known anti-diarrheal effects of *Saccharomyces boulardii*.

Thus, the present invention relates to a method of treating or preventing weight loss of patients with inflammatory bowel diseases comprising administrating to said patient an effective amount of *Saccharomyces boulardii*.

BRIEF DESCRIPTION OF THE FIGURES

FIGS. 1A, 1B and 1C represent the evolution of the weight (vertical axis, in grams) of IBD mice administered daily with 200 μl of *Saccharomyces boulardii* solutions, as a function of time (horizontal axis, in weeks).

FIG. 1A: diamond shapes represent IBD mice not administered with *S. boulardii*, black circles IBD represent mice having received a 0.1 mg/ml *S. boulardii* solution, black triangles represent mice having received a 1 mg/ml *S. boulardii* solution, crosses represent mice having received a 10 mg/ml *S. boulardii* solution, and white squares represent normal mice.

FIG. 1B: diamond shapes represent IBD mice not administered with *S. boulardii*, black circles IBD represent mice having received a 0.001 mg/ml *S. boulardii* solution, black triangles represent mice having received a 0.01 mg/ml *S. boulardii* solution, and crosses represent mice having received a 0.1 mg/ml *S. boulardii* solution.

FIG. 1C: diamond shapes represent IBD mice not administered with *S. boulardii*, black circles IBD represent mice having received a 0.001 mg/ml *S. boulardii* solution, black triangles represent mice having received a 0.1 mg/ml *S. boulardii* solution, and crosses represent mice having received a 1 mg/ml *S. boulardii* solution.

DETAILED DESCRIPTION OF THE INVENTION

Figure 1A:
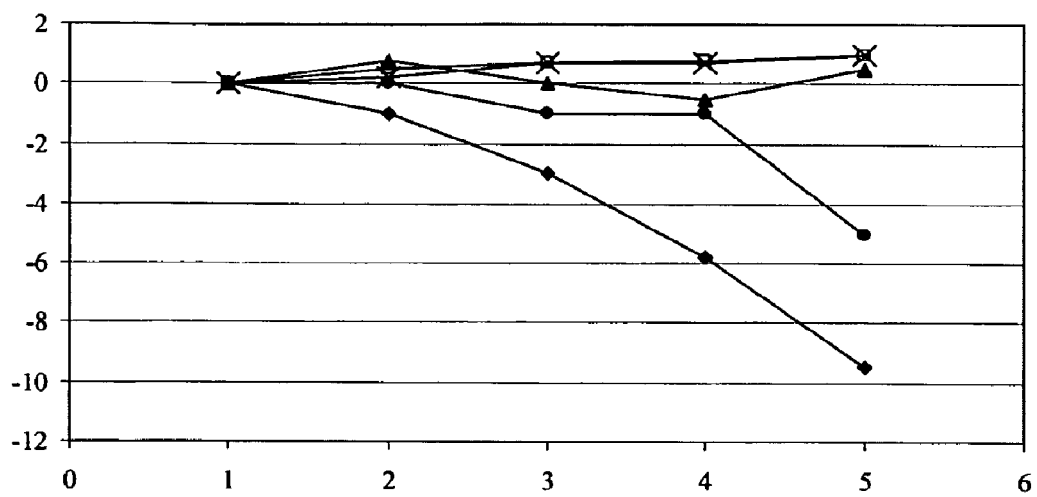
FIG. 1A, FIG. 1B and FIG. 1C

The yeast *Saccharomyces boulardii* is a variant of *Saccharomyces cerevisiae*. It is notably characterized in Mallié et al. (2001) *J. Mycol. Med.* 11:19-25. In particular, isolates of *S. boulardii* are deposited under the Budapest treaty at the Centre National de culture de Microorganismes (Institut Pasteur, Paris, France) under reference number 1-745 (Mar. 28, 1988) and at the American type Culture Collection (Rockville, USA) under reference number 74012 (Jul. 18, 1990). *Saccharomyces boulardii* is also commercially available as Ultra-Levure® (Laboratoires Biocodex, Gentilly, France).

As intended herein, inflammatory bowel diseases (IBD) are conditions characterized by chronic inflammatory lesions of the intestinal tract consecutive to an activation of the intestinal immune system. Manifestations of IBD notably comprise abdominal pain, diarrhea, anorexia and weight loss.

The present invention relates to a method of treating or preventing weight loss of patients with inflammatory bowel diseases comprising administering to said patients an effective amount of *Saccharomyces boulardii* (*S. boulardii*).

In a particular embodiment of the above defined method, the above mentioned inflammatory bowel diseases are selected from Crohn's disease, ulcerative colitis, pouchitis or indeterminate colitis.

In a more particular embodiment, the invention relates to a method as defined above of treating or preventing weight loss of patients with Crohn's disease, which comprises administering to said patients an effective amount of *S. boulardii*.

According to a preferred embodiment of the above defined method of treating or preventing weight loss of patients with inflammatory bowel diseases, *S. boulardii* is in the form of a lyophilizate.

Lyophilization, or freeze drying, is a conservation method in which yeast cells are frozen and then submitted to a sublimation of their iced water content to yield a dry yeast powder containing advantageously less than 2% water, preferably less than 1%. Lyophilizates are usually obtained by vacuum drying S. boulardii frozen concentrates. Any yeast lyophilization method known to the man pertaining to the art can be used. However, a preferred method is as follows.

Saccharomyces boulardii cells are cultured in a liquid nutritive medium (from 4700 to 9500 liters) until they reach a stationary phase, which corresponds to a cell concentration of $10\pm1\%$ (w/v). Yeast cells are then concentrated by centrifugation to yield cream-like concentrates weighing from 500 to 1300 kg depending on the initial culture volume. From 65 kg to 170 kg of a cryoprotecting 25% (w/w) lactose solution are added to the concentrates, depending on the initial culture volume. The concentrates are then freezed at −30° C. by 2.4 kg aliquots during about 18.5 hours. The frozen concentrates are lyophilizated using CS 1500 SERAIL (Argenteuil, France) automated lyophilizers or SMH 1000, SMH 1500, and SMH 3600 USIFROID (Maurepas, France) automated lyophilizers. The solid cake-like lyophilizates obtained are then grinded to yield a powder.

Advantageously, the viability and the vitality of yeast cells recovered from lyophilizates is higher than what can be obtained by other conventional conservation methods.

Thus, the present invention relates to a method of treating or preventing weight loss of patients with inflammatory bowel diseases as defined above, wherein S. boulardii is in the form of a lyophilizate such as obtained according to the following method:

culturing S. boulardii cells (ATCC 74012 or CNCM I-745) in a nutritive medium until the cells reach a stationary phase, concentrating the cultured S. boulardii cells and freezing the concentrate, vacuum drying the frozen concentrate.

In a preferred embodiment of the above defined method, S. boulardii is administered orally.

In another preferred embodiment of the above defined method S. boulardii is administered in the form of tablets, capsules, dragees, sachets or suspensions.

In yet another preferred embodiment of the above defined method, the daily dosage of S. boulardii, in particular lyophilizated S. boulardii, is from about 1 mg/kg to about 100 mg/kg and in particular of about 10 mg/kg.

In particular lyophilizated S. boulardii is administered to patients at dosages ranging from about 100 mg/day to about 1000 mg/day, and in particular at a dosage of about 750 mg/day.

In an advantageous embodiment of the above defined method, S. boulardii is administered in association with at least one other medicine intended for the prevention or the treatment of inflammatory bowel diseases, such as a medicine selected from the group constituted of corticosteroids, such as prednisolone, hydrocortisone, or budesonide, aminosalicylates, such as sulfasalazine or mesalazine, immunosuppressants, such as azathioprine or 6-mercaptopurine, methotrexate, ciclosporin, thalidomide, mycophenolate mofetil, and anti-TNFα monoclonal antibodies, such as infliximab.

The present invention also relates to the use of Saccharomyces boulardii for the manufacture of a medicament intended for the prevention or the treatment of weight loss in patients with inflammatory bowel diseases.

EXAMPLE 1

Prevention of Weight Loss by Saccharomyces boulardii in an Animal Model of Inflammatory Bowel Disease (IBD)

The animal model which was used in the following experiments was initially described by Powrie et al. (1993) Int. Immunol. 5:1461-1471 and has been widely in use since then (Powrie et al. (1994) Immunity 1:553-562; Groux et al. (1997) Nature 389:737-742) for studies focusing on inflammatory bowel diseases, such as Crohn's disease.

Briefly, immunodeficient mice of the C.B-17 scid type are intraperitoneally injected with approximately $2.5\,10^5$ CD4+ T cells which highly express the CD45RB molecule (CD4+ CD45RB$^{hi}$ T cells), the CD4+CD45RB$^{hi}$ T cells being isolated by using a FACS from BALB/C mice.

These mice, hereafter designated "IBD mice", present bowel lesions similar to those induced by Crohn's disease in association to a substantial weight loss.

The study of the effects of the oral administration of lyophilized Saccharomyces boulardii on the weight of IBD mice was undertaken by the Inventors. The evolution of weight variation parallels IBD evolution.

Groups of 5 IBD mice were respectively force fed daily with 200 μl of PBS solutions (Phosphate Buffer Saline) containing lyophilized Saccharomyces boulardii (Ultra Levure®, Laboratoires Biocodex, France) at concentrations ranging from 0 to 10 mg/ml for 4 weeks. A non-pathogenic control group (i.e. not injected with CD4+CD45RB$^{hi}$ T cells) was also included in the study.

Figure 1B:
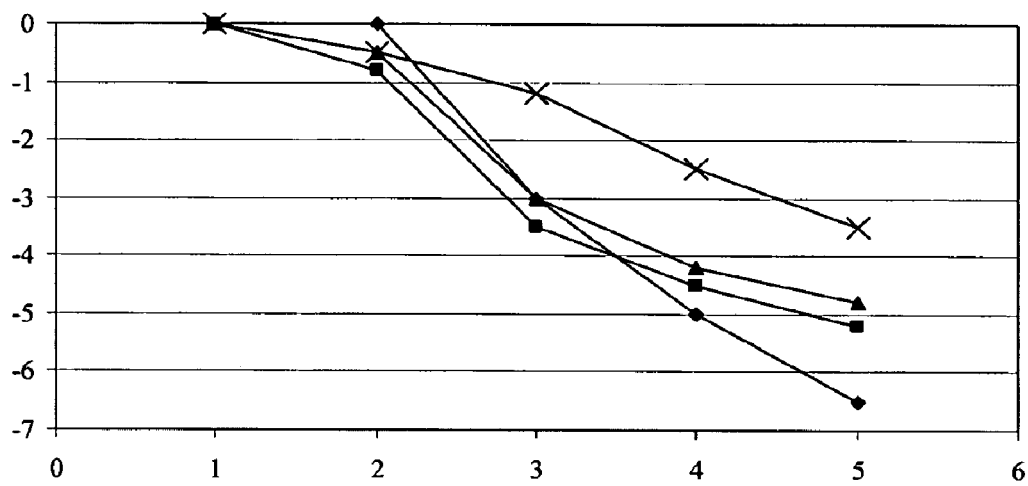
Figure 1C:
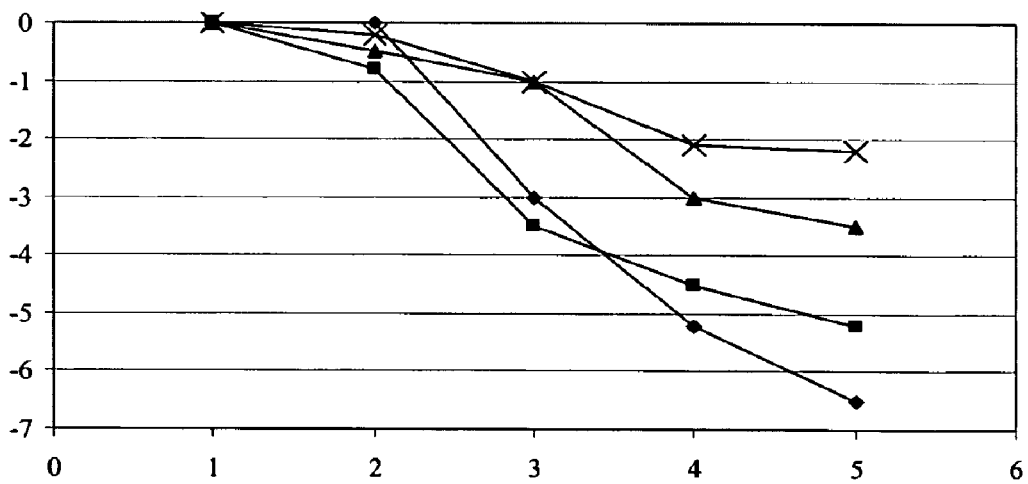

The results obtained from 3 independent experiments are presented in the following Tables 1, 2 and 3 and in the corresponding FIGS. 1A, 1B and 1C.

TABLE 1 effect on weight variation of S. boulardii administration to IBD mice (experiment 1)

| Group | Concentration of S. boulardii solution (quantity administered) | Weight variation after 4 weeks | |
|---|---|---|---|
| Control | — | +1 g | +5 |
| IBD mice | 0 mg/ml (0 mg/kg) | −9.5 g | −47.5 |
| IBD mice | 0.1 mg/ml (1 mg/kg) | −5 g | −25 |
| IBD mice | 1 mg/ml (10 mg/kg) | +0.5 g | −2.5 |
| IBD mice | 10 mg/ml (100 mg/kg) | +1 g | +5 |

TABLE 2 effect on weight variation of S. boulardii administration to IBD mice (experiment 2)

| Group | Concentration of S. boulardii solution (quantity administered) | Weight variation after 4 weeks | |
|---|---|---|---|
| IBD mice | 0 mg/ml (0 mg/kg) | −6.5 g | −32.5 |
| IBD mice | 0.001 mg/ml (0.01 mg/kg) | −5.2 g | −26 |
| IBD mice | 0.01 mg/ml (0.1 mg/kg) | −4.8 g | −24 |
| IBD mice | 0.1 mg/ml (1 mg/kg) | −3.5 g | −17.5 |

TABLE 3 effect on weight variation of *S. boulardii*
administration to IBD mice (experiment 3)

| Group | Concentration of S. boulardii solution (quantity administered) | Weight variation after 4 weeks | |
|---|---|---|---|
| IBD mice | 0 mg/ml (0 mg/kg) | −6.5 g | −32.5 |
| IBD mice | 0.001 mg/ml (0.01 mg/kg) | −5.2 g | −26 |
| IBD mice | 0.1 mg/ml (1 mg/kg) | −3.5 g | −17.5 |
| IBD mice | 1 mg/ml (10 mg/kg) | −2.2 g | −11 |

The results obtained by the Inventors indicate that *S. boulardii* administration to IBD mice results in a potent reduction in weight loss. Thus, patients suffering from inflammatory bowel diseases, such as Crohn's disease could benefit from *S. boulardii* administration, at doses ranging from 1 mg/kg to 100 mg/kg, to reduce weight loss.

Besides, it is to be noted that parallel studies carried on normal mice administered with the above *S. boulardii* solutions did not show any adverse effect of *S. boulardii* administration, even with high quantities

EXAMPLE 2

Prevention of Bowel Inflammation by *Saccharomyces boulardii* in Parallel with Prevention of Weight Loss in an Animal Model of Inflammatory Bowel Disease Since it was shown by the Inventors that lyophilized *S. boulardii* administration to IBD mice has a beneficial effect on the limitation of weight loss, they further investigated to determine if *S. boulardii* had a favorable impact on the inflammatory status of the colon.

Colonic sections taken from IBD mice treated as described in Example 1 were graded from 0 to 5, in a blind study, relatively to their inflammatory status.

The following grades were affected to each section analyzed:

Grade 0: normal;

Grade 1: slight scattered mucosal leukocyte infiltration optionally associated to a slightly hyperplastic epithelium;

Grade 2: modest scattered or grouped leukocyte infiltration reaching sub-mucosa associated to an eroded and a slightly hyperplastic epithelium;

Grade 3: slight transmural inflammatory infiltrations, usually associated to ulcerations and a slight hyperplasia;

Grade 4: strong infiltrations, usually transmural, associated to ulcerations and a strong hyperplasia;

Grade 5: strong transmural inflammation associated to severe ulcerations and an intestinal gland loss.

The results obtained from 3 independent experiments are presented in the following Tables 4, 5 and 6:

TABLE 4 effect on bowel inflammation of *S. boulardii*
administration to IBD mice (experiment 1)

| Group | Concentration of S. boulardii solution (quantity administered) | Clinical grade of colonic section after 4 weeks |
|---|---|---|
| IBD mice | 0 mg/ml (0 mg/kg) | 4 ± 0.5 |
| IBD mice | 0.1 mg/ml (1 mg/kg) | 3.5 ± 0.2 |
| IBD mice | 1 mg/ml (10 mg/kg) | 2.5 ± 0.5 |
| IBD mice | 10 mg/ml (100 mg/kg) | 2.2 ± 0.3 |

TABLE 5 effect on bowel inflammation of *S. boulardii*
administration to IBD mice (experiment 2)

| Group | Concentration of S. boulardii solution (quantity administered) | Clinical grade of colonic section after 4 weeks |
|---|---|---|
| IBD mice | 0 mg/ml (0 mg/kg) | 4.2 ± 0.4 |
| IBD mice | 0.001 mg/ml (0.01 mg/kg) | 4.5 ± 0.4 |
| IBD mice | 0.01 mg/ml (0.1 mg/kg) | 4.1 ± 0.8 |
| IBD mice | 0.1 mg/ml (1 mg/kg) | 3.3 ± 0.7 |

TABLE 6 effect on bowel inflammation of *S. boulardii*
administration to IBD mice (experiment 3)

| Group | Concentration of S. boulardii solution (quantity administered) | Clinical grade of colonic section after 4 weeks |
|---|---|---|
| IBD mice | 0 mg/ml (0 mg/kg) | 4.2 ± 0.6 |
| IBD mice | 0.01 mg/ml (0.1 mg/kg) | 4 ± 0.5 |
| IBD mice | 0.1 mg/ml (1 mg/kg) | 2.4 ± 0.4 |
| IBD mice | 1 mg/ml (10 mg/kg) | 2.1 ± 0.7 |

The results obtained by the Inventors indicate that *S. boulardii* administration to IBD mice results in a significant reduction of colon inflammation, which correlates with the reduction in weight loss observed in Example 1. Furthermore, the dose of lyophilized *S. boulardii* effective at reducing inflammation is determined as ranging from 1 mg/kg to 100 mg/kg.

EXAMPLE 3

Prevention of IFN-γ Secretion by *Saccharomyces boulardii* in an Animal Model of Inflammatory Bowel Disease Following the finding that *S. boulardii* had a favorable impact on the prevention of weight loss and on the inflammatory status of the colon, the Inventors further investigated the effect of *S. boulardii* on the production of the Th1-secreted inflammatory cytokine IFN-γ by cells of the colon.

Briefly, colonic T cells were purified from inflammatory colonic sections taken from IBD mice treated as described in Example 1 and were cultured in the presence of mitogens. IFN-γ concentration in the cultures supernatant of the purified T cells was then measured by ELISA.

The results obtained from 3 independent experiments are presented in the following Tables 7, 8 and 9:

TABLE 4 effect on IFN-γ secretion of S. boulardii administration to IBD mice (experiment 1)

| Group | Concentration of S. boulardii solution (quantity administered) | IFN-γ concentration (ng/ml) |
|---|---|---|
| IBD mice | 0 mg/ml (0 mg/kg) | 33 |
| IBD mice | 0.1 mg/ml (1 mg/kg) | 0 |
| IBD mice | 1 mg/ml (10 mg/kg) | 0 |
| IBD mice | 10 mg/ml (100 mg/kg) | 0 |

TABLE 5 effect on IFN-γ secretion of S. boulardii administration to IBD mice (experiment 2)

| Group | Concentration of S. boulardii solution (quantity administered) | IFN-γ concentration (ng/ml) |
|---|---|---|
| IBD mice | 0 mg/ml (0 mg/kg) | 29 |
| IBD mice | 0.001 mg/ml (0.01 mg/kg) | 32 |
| IBD mice | 0.01 mg/ml (0.1 mg/kg) | 28 |
| IBD mice | 0.1 mg/ml (1 mg/kg) | 9 |

TABLE 6 effect on IFN-γ secretion of S. boulardii administration to IBD mice (experiment 3)

| Group | Concentration of S. boulardii solution (quantity administered) | IFN-γ concentration (ng/ml) |
|---|---|---|
| IBD mice | 0 mg/ml (0 mg/kg) | 18 |
| IBD mice | 0.01 mg/ml (0.1 mg/kg) | 16 |
| IBD mice | 0.1 mg/ml (1 mg/kg) | 1 |
| IBD mice | 1 mg/ml (10 mg/kg) | 3 |

The results obtained by the Inventors indicate that S. boulardii administration to IBD mice results in a significant reduction of IFN-γ secretion by colonic T cells of the Th1 subtype, which correlated with the observed reduction in inflammation and prevention of weight loss. As seen in Examples 1 and 2, the effective dose of lyophilized S. boulardii ranges from 1 mg/kg to 100 mg/kg.

All the cited publications are incorporated herein by reference.

The invention claimed is:

1. A method of treating weight loss and reducing colonic interferon-gamma (IFN-γ) secretion in a patient having an inflammatory bowel disease (IBD) comprising administering to the patient an effective amount of Saccharomyces boulardii (S. boulardii) to reduce weight loss and to reduce colonic IFN-γ secretion, wherein the patient's weight loss is due to chronic inflammatory lesions of the patient's intestinal tract consecutive to an activation of the intestinal immune system.

2. The method according to claim 1, wherein the patient has Crohn's disease.

3. The method according to claim 1, wherein S. boulardii is in the form of a lyophilisate.

4. The method according to claim 1, wherein S. boulardii is in the form of a lyophilisate obtained by culturing S. boulardii cells, as deposited with the American Type Culture Collection (ATCC) as Accession Number 74012 or Accession Number CNCM I-745, in a nutritive medium until the cells reach a stationary phase; concentrating the cultured S. boulardii cells to obtain a concentrate and freezing the concentrate to obtain a frozen concentrate; and vacuum drying the frozen concentrate.

5. The method according to claim 1, wherein S. boulardii is administered orally.

6. The method according to claim 1, wherein S. boulardii is administered in the form of tablets, capsules, dragees, sachets or suspensions.

7. The method according to claim 1, wherein the S. boulardii is administered as a daily dosage of about 1 mg/kg to about 100 mg/kg.

8. A method of treating weight loss and reducing colonic IFN-γ secretion in a patient having Crohn's disease comprising
administering to the patient an effective amount of Saccharomyces boulardii (S. boulardii) to reduce weight loss and to reduce colonic IFN-γ secretion, wherein said Crohn's disease is of a severity to induce weight loss.

9. The method according to claim 8, further comprising administering to said patient a drug selected from the group consisting of corticosteroids, prednisolone, hydrocortisone, budesonide, aminosalicylates, sulfasalazine, mesalazine, immunosuppressants, azathioprine, 6-mercaptopurine, methotrexate, ciclosporin, thalidomide, mycophenolate mofetil, anti-tumor necrosis factor(anti-TNFα) monoclonal antibodies, and infliximab.

10. The method according to claim 8, wherein S. boulardii is in the form of a lyophilisate.

11. The method according to claim 8, wherein S. boulardii is administered orally.

12. The method according to claim 8, wherein the S. boulardii are ATCC Accession Number 74012 or ATCC Accession Number CNCM I-745 S. boulardii cells.

13. The method of claim 7, wherein the daily dosage is about 10 mg/kg.

* * * * *